United States Patent [19]

Bachmann et al.

[11] Patent Number: 5,537,754
[45] Date of Patent: Jul. 23, 1996

[54] EXTENSOMETER AND SUPPORT FOR AN EXTENSOMETER

[75] Inventors: Volker Bachmann, St. Augustin; Claudio Dalle Donne, Cologne, both of Germany

[73] Assignee: Deutsche Forschungsanstalt fur Luft-und Raumfahrt e.V., Bonn, Germany

[21] Appl. No.: 335,065

[22] Filed: Nov. 4, 1994

[30] Foreign Application Priority Data

Nov. 7, 1993 [DE] Germany .......................... 43 38 005.0

[51] Int. Cl.⁶ .................................................. G01B 7/16
[52] U.S. Cl. ................................................. 33/787; 73/781
[58] Field of Search .............................. 73/781; 33/783, 33/784, 787, 788, 789, 790, DIG. 1, DIG. 13

[56] References Cited

U.S. PATENT DOCUMENTS

| | | | |
|---|---|---|---|
| 1,999,075 | 4/1935 | Bauer et al. | 33/787 |
| 2,099,896 | 11/1937 | Kinzel | 33/788 |
| 2,495,797 | 1/1950 | Whitlock et al. | 33/DIG. 13 |
| 3,001,291 | 9/1961 | Sjostrom | 33/787 |
| 3,660,904 | 5/1972 | Steele et al. | 33/788 |
| 4,223,443 | 9/1980 | Bachmann et al. | 33/DIG. 13 |
| 4,527,335 | 7/1985 | Meline | 33/787 |
| 4,939,445 | 7/1990 | Meline et al. | 33/789 |

FOREIGN PATENT DOCUMENTS 2816444  10/1979  Germany .

*Primary Examiner*—Thomas B. Will
*Assistant Examiner*—G. Bradley Bennett
*Attorney, Agent, or Firm*—Loeb & Loeb

[57] ABSTRACT

The extensometer comprises a basic body (18) which carries two tap legs (12) which abut a specimen (16) to be measured so as to be frictionally locked thereto. Due to the frictional contact, the tap legs (12) move relative to each other when the specimen is subjected to external stresses. Via a signal transmitter (24), this movement of the tap legs (12) is detected. The extensometer (10) is floatingly supported by introducing gas in the clearance between a baffle body (36) connected to the extensometer (10) and a stationary support member (28) toward the baffle body (36). On the one hand, the upbuilding gas cushion presses the extensometer (10) with its tap legs (12) against the specimen (16) so as to be frictionally locked thereto and, on the other hand, permits pivoting of the extensometer (10) corresponding to the movement of the measuring points.

12 Claims, 2 Drawing Sheets

EXTENSOMETER AND SUPPORT FOR AN EXTENSOMETER

BACKGROUND OF THE INVENTION

The invention relates to an extensometer comprising a basic body, at least two tap legs adapted to be pressed against a specimen so as to be frictionally locked thereto, the tap legs being mounted to the specimen such that they are movable relative to each other, a signal transmitter being mechanically coupled to at least one tap leg and providing an output signal representing the amount of a relative movement of the tap legs, and a support device for supporting the basic body and pressing the tap legs against the specimen. Further, the invention relates to a support for an extensometer comprising tap legs.

In material and/or component tests, extension sensors (so-called extensometers) are used to detect the dependence between an external stress of a specimen and the local deformation thereof. Such an extensometer, for example, is described in DE 28 16 444 C3. The known extensometer comprises a basic body on which at least two tap legs are supported. With its tap legs, the extensometer is pressed against the specimen to be tested so as to be frictionally locked thereto. The specimen is deformed by extending, compressing or other external stresses, which leads to a relative movement of the two tap legs. At least one of the two tap legs is coupled to a signal transmitter in the form of an electromechanical transformer. In the case of the extensometer of DE 28 16 444 C3, the transformer is a wire strain gauge strip which is mounted on a leaf spring connecting the two tap legs. The signal transmitter normally used with extensometers, however, may also operate inductively or capacitively. When performing tests with extensometers, it is to be considered that the tap legs are firmly connected to the specimen and frictionally locked thereto. For this purpose, the known extensometer is retained at the specimen itself by clamping elements. Other known extensometers use retaining devices at which the basic body of the extensometer is retained and which firmly press the extensometer with its tap legs against the specimen.

The displacement distances measured by an extensometer amount to from some micometers to some 10 mm. These small displacement distances require highly sensitive and accurately measuring extensometers.

The main problem with the use of extensometers is that the deformation of the specimen due to the external stress is not known in advance. Namely, if the two contact points at which the tap legs abut the specimen do not move along the straight line defined by the two contact points, then the extensometer is slightly rotated via the tap legs during the deformation of the specimen, and the extensometer is thus canted. Due to the canting, the two tap legs can no longer move freely relative to each other, which falsifies the measuring result.

SUMMARY OF THE INVENTION

It is the object of the present invention to provide an extensometer for measuring extensions on specimens which permits distance measuring of the measuring points unaffected by the fastening of the extensometer, i.e. without any feedback.

In order to solve this object, the invention suggests an extensometer of the afore-mentioned kind wherein the support device permits a freely movable floating support of the extensometer upon the tap legs' contact with the specimen.

In the case of the extensometer according to the invention, the support device is provided with a mechanical decoupling between the extensometer and a retaining device carrying the support device. This means that the support device and the retaining device do not comprise any connection to the specimen; particularly, neither the support device nor the retaining device are retained at the specimen. In spite of this mechanical decoupling, the pressing force acting upon the extensometer in the support device is so high that the extensometer tap legs abut on the specimen so as to be locked by force engagement (due to frictional forces or due to complementary shape of the parts engaged). Due to its freely movable floating support, the extensometer can orient corresponding to the deformation of the specimen during the measurement. The tap legs which abut on the specimen so as to be frictionally locked thereto transfer the movement of the two measuring points to the basic body which, due to the support according to the invention, is not firmly clamped but freely movable and orients corresponding to the movement of the tap legs. The extensometer supported according to the invention thus follows the measuring point traveling, even if, what occurs most often, the measuring points do not move along the straight line through the two contact points between tap legs and specimen.

In an advantageous development of the invention, it is provided that the extensometer is pneumatically, hydraulically or magnetically supported in the support device. By pneumatic support, the support of the extensometer on an air cushion is meant, whereas a hydraulic support is a liquid pad on which the extensometer rests or via which the extensometer is pressed against the specimen. A magnetic support, for example, is effected by building up a magnetic field between the extensometer and the retaining device carrying the support device, which generates a force onto the extensometer repulsing it from the support device, due to which force the extensometer is pressed against the specimen with its tap legs. The pneumatic as well as the hydraulic as well as the magnetic support each include the mechanical decoupling of extensometer and retaining device in the support device.

Preferably, the support device comprises a baffle body connected to the basic body and/or to at least one tap leg and comprising a baffle surface against which gas from at least one gas outlet is directed. This gas outlet is, in the simplest case, a gas nozzle or the end of a gas conduit. From the gas outlet, the gas flows against the baffle surface and thus presses the extensometer with its tap legs against the specimen via the baffle body. Advantageously, several gas outlets, preferably three gas outlets arranged in the shape of a triangle or four gas outlets arranged in the shape of a quadrangle are provided as spread over the baffle surface. The support described herein is a pneumatic one, the hydraulic support functions correspondingly by liquid streams being directed toward the baffle surface.

Preferably, a gas pad carrying the extensometer and pressing against the specimen is built up between two closely adjacent, substantially parallel surfaces in the support device. For this purpose, the support device comprises a support member comprising an inner surface facing the baffle surface and being substantially parallel thereto; this support member has no contact with either the basic body or the tap legs held by a retaining device. Gas directed toward the baffle surface flows through the support member into the laterally open clearance between the support member and the baffle body. As a result, a gas pad is built up between the inner surface of the support member and the baffle surface. Due to the fact that gas from preferably several outlets is supplied to this clearance through the support member, tilting of the extensometer is prevented. For as soon as the extensometer tilts, the clearance between the inner surface of the support member and the baffle surface narrows, this event is opposed by a pressure rise of the supplied gas in the region of the narrowing clearance. Advantageously, the support member is supported on the retaining device so as to be particularly freely movable and/or pivotable, so that also the extensometer can be oriented via the orientation of the support member. Due to the movability, pivotability and/or tiltability of the support member relative to the retaining device, a self-orientation of the support member is given.

Preferably, the basic body of the extensometer is coupled to a rotation angle sensor outputting a signal representing a rotation of the basic body. This rotation angle sensor permits to detect a rotation of the extensometer during the measurement. Thus, a continuous determination of the measuring point coordinates is possible; from the rotation of the extensometer and the movement of the tap legs, the migration of the measuring points, starting from the beginning of the experiment, can be exactly reconstructed. Advantageously, a rotation angle sensor is utilized which permits a contactless rotation of the extensometer, so that the free movement of the extensometer is not affected by the rotation angle sensor and the fastening thereof.

With the support of the extensometer according to the invention, it is also possible for the extensometer to follow when moving the specimen surface away from the support device. Advantageously, the gas pressure at the gas outlet is continuously detected therefor by means of a gas pressure sensor. The output signal of the gas pressure sensor is supplied to a drive device which, in turn, transmits a drive signal to an actuator which automatically changes the distance of the gas outlet from the baffle surface. A decreasing gas pressure at the gas outlet means that the baffle surface moves away from the gas outlet, because, for instance, the specimen surface (due to the outer stresses of the specimen) moves away from the gas outlet. The decreasing gas pressure is announced to the drive device which then drives the actuator to decrease the distance between gas outlet and baffle surface. Vice versa, the actuator would increase the distance between gas outlet and baffle surface if the gas pressure increased. By means of this pressure-dependent control, the support device can also follow greater changes in thickness or distance.

The preferred embodiments of the invention mentioned above correspondingly also refer to the case that instead of a pneumatic support of the extensometer, a hydraulic one is used. Therefore, the term "gas" or "gaseous" etc. can be replaced by "fluid" (corresponds to gaseous and/or liquid medium) in the above description text.

BRIEF DESCRIPTION OF THE DRAWINGS

Hereinafter, two embodiments of the invention are explained in detail with respect to the drawings, in which.

DESCRIPTION OF THE PREFERRED EMBODIMENTS

Figure 1:
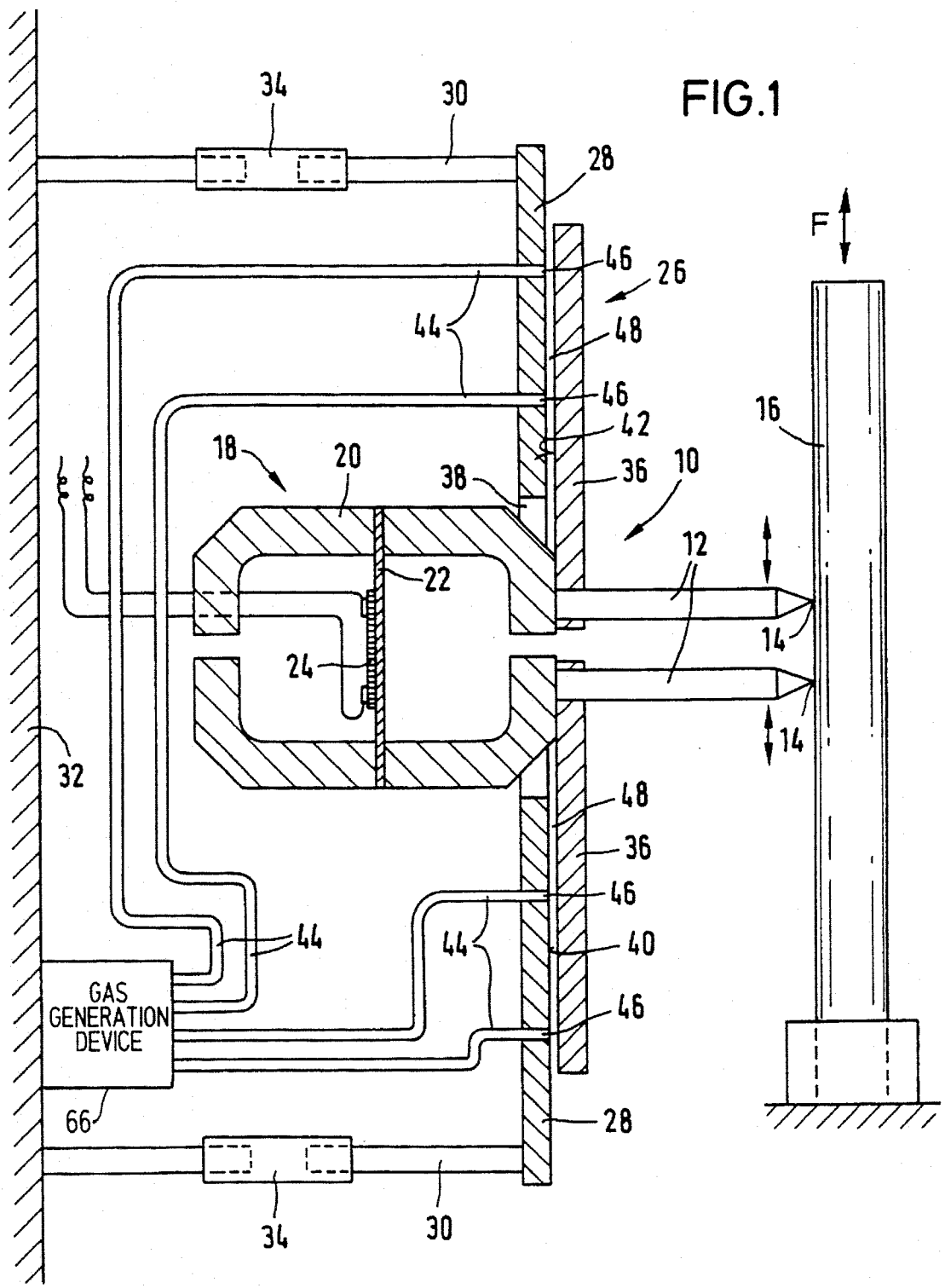
FIG. 1 is a side view of a first embodiment of an extensometer supported according to the invention and vertically oriented.

FIG. 1 shows a first embodiment of an extensometer 10 supported according to the invention. The extensometer 10 comprises two tap legs or points 12 which have their pointed ends 14 abutting a—in this case cylindrical—specimen 16 so as to be frictionally locked to the outer surface thereof. The specimen 16 is subjected to external mechanical stresses F (tension or compression, shown by means of a double arrow in the Figures), and via the tap legs 12, the extensometer 10 detects the material movement of the specimen 16 which results from the external stress.

The tap legs 12 of the extensometer 10 are rigidly connected to a two-part basic body 18. The basic body 18 comprises two spaced parts 20 which are symmetrically arranged with respect to each other and are, in side view, substantially C-shaped. The two C-shaped parts 20 are movably connected via a leaf spring. At one side of the leaf spring 22, a wire strain gauge strip 24 is attached whose electrical connection lines are connected to a signal evaluation and display device (not shown).

A pneumatic support device 26 is provided for supporting the extensometer 10 and for pressing the extensometer 10, with the tap legs 12 thereof, against the specimen 16. The support device 26 comprises a support member in the form of a plate 28 which is fixed by means of several retaining bars 30 of a retaining device 32, which retaining bars are variable in length. In the drawing, the length changeability of the retaining bars 30 is intended to be indicated at 34.

Next to the plate-shaped support member 28, the support device 26 comprises two baffle bodies in the form of plates 36. One plate-shaped baffle body 36, respectively, is connected to one C-shaped part 20 of the basic body 18, and actually at the ends of the C-shaped parts 20 carrying the tap legs 12. In the plate-shaped support member 28, there is a central recess 38 through which the C-shaped part 20 extends, as shown in FIG. 1. The plate-shaped baffle bodies 36 are arranged substantially in parallel to the plate-shaped support member 28, the inner surface 40 of the support member facing the plate-shaped baffle bodies 36 being opposite the baffle surfaces 42 of the plate-shaped baffle bodies 36 facing the support member. The entire equipment is set such that a narrow gap of some few millimeters arises between the plate-shaped baffle bodies 36 and the plate-shaped support member 28 when the extensometer 10, with its tap legs 12, abuts the specimen 16 so as to be frictionally locked thereto.

Gas-bearing lines shown at 44 and being connected to a gas generation source not shown in FIG. 1 are led through the support member 28. Several gas lines 44 end at 46, i.e. respectively opposite the baffle surfaces 42 of both plate-shaped baffle bodies 36. The gas from the gas lines 44 emerging at the gas outlets 46 flows against the baffle surfaces 42 and from there, it spreads into the entire clearance 48 from which it emerges via the laterally open boundaries between support member 28 and baffle bodies 36. Thus, a gas pad is formed in clearance 48, which presses the extensometer 10, with its tap legs 12, firmly against the specimen and frictionally locked thereto via the baffle bodies 36.

Due to the external stresses acting upon the specimen 16, the latter experiences material movements which lead to a movement of the measuring points (contact points between the pointed tips 14 of the tap legs 12 and the surface of the specimen 16). Because of the frictional locking, the extensometer 10 is quasi rigidly coupled to the specimen 16 via its tap legs 12. Due to the deformation of the specimen 16, the case may arise that the contact points do not move along the straight line extending therethrough but move along other, if necessary, curved lines. The extensometer 10 according to the invention shown in FIG. 1 follows this movement of the contact or measuring points on the surface of the specimen 16, since the air cushion support in the support device 26 also permits rotation of the extensometer 10 and also displacements of the extensometer 10. The fastening of the extensometer 10 is thus decoupled from the extensometer 10 itself, so that the fastening of the extensometer 10 has no feedback effects on the measurement. Accordingly, the measurement is highly accurate and exactly represents the actual distance of the two measuring points in each phase of the measurement.

Moreover, the gas laterally emerging from the clearance 48 shields the sensitive electromechanical transformer unit, i.e. the wire strain gauge strip 24, from heat to which the specimen 16, depending on the experiments to be carried out, is subjected to examine the elongation behavior.

Figure 2:
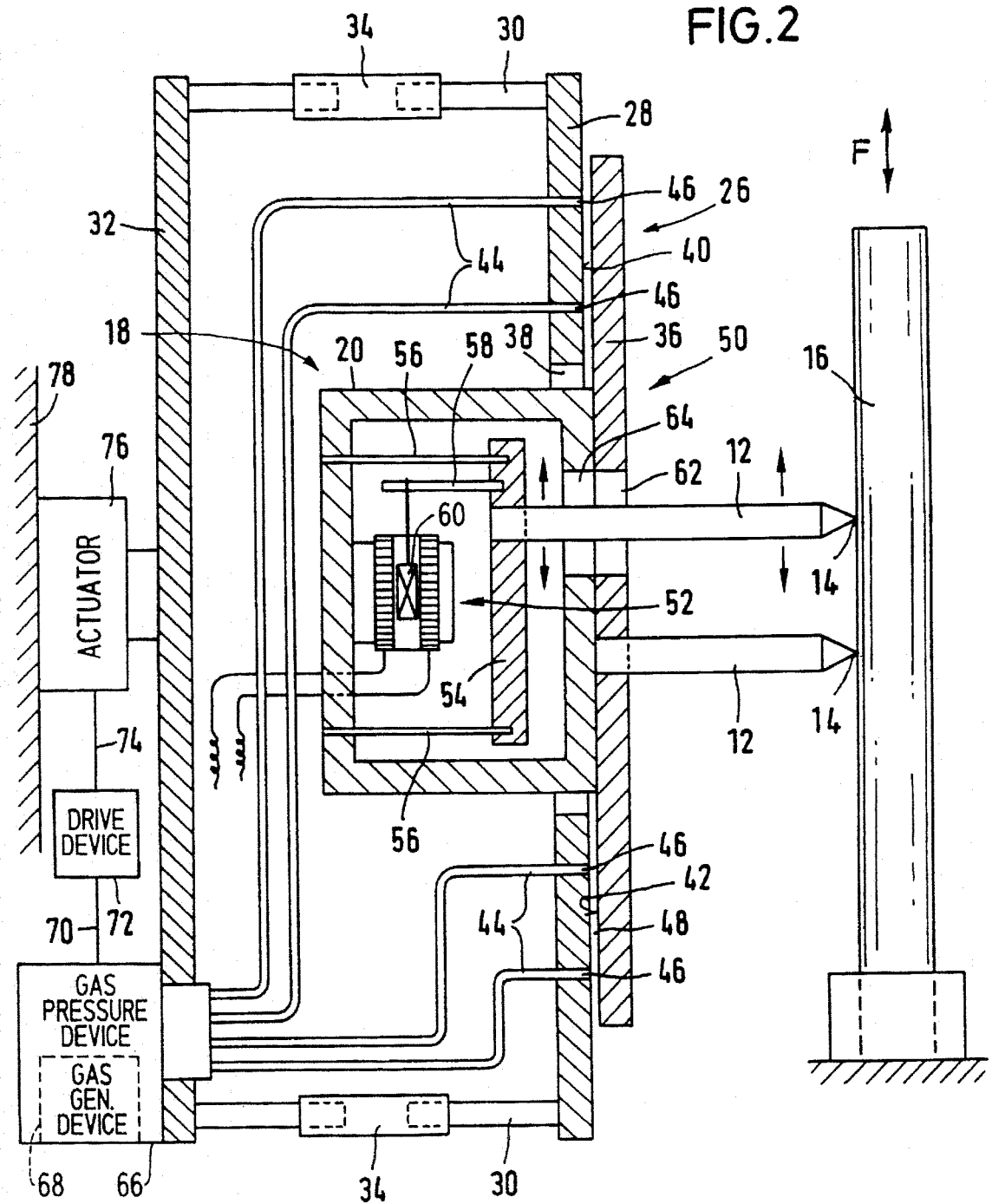
FIG. 2 is a side view of a second embodiment of an extensometer supported according to the invention and also vertically oriented.

FIG. 2 shows, in side view, a second embodiment of an extensometer 50 supported according to the invention. As far as the individual parts of the extensometer 50 correspond to these of the extensometer 10 according to FIG. 1, they are indicated with the same reference numerals as in FIG. 1. In contrast to the extensometer 10, the extensometer 50 comprises an inductive measuring signal transformer 52. This inductive measuring signal transformer 52 is fastened in the interior of the basic body 18 provided with a rigid, substantially rectangular frame 20. While one of the two tap legs 12 is fixedly and rigidly connected to the frame 20, the second tap leg 12 is retained by a retaining member 54 being arranged in the interior of the basic body 18. Via two leaf springs 56, this retaining member 54 is connected to the frame 20 of the basic body 18. On the retaining member 54, a finger 58 is arranged which carries a pin 60 which, in turn, is immersed into the inductive measuring signal transformer 52 and, depending on the degree of immersion, changes the inductivity thereof. The tap leg 12 connected to the retaining member 54 passes through an opening in the frame 20 and extends parallel to the second tap leg 12. A movement (extension or compression) of the specimen 16 leads to a relative movement of the two tap legs 12 which—bending the two leaf springs 56 also leads to a more or less deep immersion of the pin 60 into the measuring signal transformer 52 which, in turn, outputs a corresponding output signal (the evaluation and display device for the measuring signal transformer 52 is not shown in FIG. 2).

Similarly to the embodiment according to FIG. 1, the support device consists of two plate-shaped elements, namely the support member 28 and the baffle body 36 connected to the frame 20 of the basic body 18. The support member 28 is carried via the length-variable retaining bars 30 of the retaining device 32. The basic body 18 partially passes through the central recess 38 in the plate-shaped support member 28. The gas lines 44 end at 46 in the plate-shaped support member 28, four such gas lines in all being provided as arranged in a quadrangle (merely two gas lines 44 can be recognized in FIG. 2).

The function mode of the support device 26 exactly corresponds to that of FIG. 1; the air pad building up due to the gas supply between the supporting member 28 and the baffle body 36 presses the extensometer 50 with the tap legs 12 thereof via the baffle body 36 against the specimen 16 so as to be frictionally locked thereto. In the baffle body 36, there is a recess 62 being in alignment with the recess 64 in the frame 20. The movable tap leg of the extensometer 50 extends through these two openings 62 and 64.

The gas lines 44 which end at 46 facing the baffle surface 42 of the baffle body 36 are connected to a gas generation device 66. The extensometer 50 comprises four such gas lines 44 which are arranged at the four corners of a quadrangle and end in the support member 28. The gas generation device 66 is provided with a gas pressure sensor 68 which measures the gas pressure in the gas lines 44. The output signal of the gas pressure sensor 68 is supplied to a drive device 72 via a signal line 70. Via a signal line 74, the output of the drive device 72 is connected to an actuator 76 which is fastened to a support device and moves the entire retaining device 32 with the support member 28 back and forth in the direction of the extension of the tap legs 12.

By means of the control device described herein and consisting of the gas pressure sensor 68, the drive device 72, and the actuator 76, it is possible for the support device 78 to follow the movement of the extensometer 50 during measurement. Such a movement of the extensometer 50 in the direction of the extension of its tap legs 12 is by no means impossible and, among other things, depends on the entire deformation of the specimen 16. This means, if the specimen 16 moves away from the support member 28 during measurement, the clearance 48 between the support member 28 and the baffle member 36 increases since the extensometer 50 remains pressed to the specimen 16 with its tap legs 12. The enlargement of the clearance 46 results in a drop of pressure of the gas in the gas lines 44, which is detected by the gas pressure sensor 68. The drop of pressure is announced to the drive device 72 which thereupon drives the actuator 76 to let the retaining device 32 follow, i.e. to move the retaining device 32 toward the specimen 16. In the reverse case, the clearance 48 decreases when the specimen 16 moves toward the support member 28. The narrowing of the clearance 48 results in a pressure rise in the gas lines 44, which the gas pressure sensor 68 announces to the drive device 72 which thereupon drives the actuator 76 to return the retaining device 32.

We claim:

1. An extensometer, comprising a basic body, at least two tap legs for being pressed against a specimen, the tap legs being mounted to the basic body so as to be movable relative to each other, a signal transmitter which is mechanically coupled to at least one tap leg and provides an output signal representing the amount of a relative movement of the tap legs, and a support device for supporting the basic body and pressing the tap legs against the specimen, wherein the support device is configured such that the basic body is floatingly arranged so as to be freely movable when the tap legs contact the specimen.

2. The extensometer of claim 1, characterized in that the support device comprises a pneumatic, hydraulic or magnetic support.

3. The extensometer of claim 1, characterized in that the support device comprises a baffle body connected to at least one of the basic body and the at least one tap leg and comprising a baffle surface against which gas from at least one gas outlet flows in a directed manner.

4. The extensometer of claim 3, characterized in that the support device comprises a support member with an inner surface facing the baffle surface and being substantially parallel thereto, the support member being retained by a retaining device without having contact with the basic body and without having contact with the tap legs, and that gas directed to the baffle surface of the baffle body flows through the support member into the laterally open clearance between the support member and the baffle body.

5. The extensometer of claim 3, characterized in that from each of several gas outlets, there is a gas flow which flows against the baffle surface.

6. The extensometer of claim 5, characterized in that the support member is at least one of adjustable in its position and retained freely movable on the retaining device.

7. The extensometer of claim 3, characterized in that a gas pressure sensor for detecting the gas pressure at the gas outlet and an actuator for automatically changing the distance between the gas outlet and the baffle surface are provided, and that the gas pressure sensor and the actuator are connected to a drive device for driving the actuator to reduce the distance between the gas outlet and the baffle surface upon decreasing gas pressure at the gas outlet and to increase the distance between the gas outlet and the baffle surface upon increasing gas pressure at the gas outlet.

8. A support for an extensometer comprising tap legs, comprising a support body connectable to the extensometer and comprising a support surface facing away from the tap legs, and a device for pneumatically, hydraulically or magnetically supporting the support body and for pressing the extensometer with its tap legs toward a specimen to be measured.

9. The support of claim 8, characterized in that the device for supporting the support body comprises a gas flow generation device with at least one gas outlet from which gas flows against the support surface in a directed manner.

10. The support of claim 9, characterized in that the at least one gas outlet is arranged in a support member which comprises a substantially parallel support surface facing the support surface of the support body and is retained by a retaining device.

11. The support of claim 10, characterized in that the support member is at least one of adjustable in its position and retained at the retaining device so as to be freely movable.

12. The support of claim 9, characterized in that a gas pressure sensor for detecting the gas pressure in the gas outlet and an actuator for automatically changing the distance between the gas outlet and the support surface of the support body are provided, and that the gas pressure sensor and the actuator are connected to a drive device for driving the actuator to decrease the distance between the gas outlet and the support surface of the support body upon decreasing gas pressure at the gas outlet and to increase the distance between the gas outlet and the support surface of the support body upon increasing gas pressure at the gas outlet.

* * * * *